United States Patent [19]

Brouhard

[11] 4,454,872

[45] Jun. 19, 1984

[54] TOE PROTECTOR FOR AN ORTHOPEDIC FOOD CAST

[76] Inventor: Ronald R. Brouhard, 7033 SE. 66th, Portland, Oreg. 97206

[21] Appl. No.: 444,835

[22] Filed: Feb. 4, 1983

[51] Int. Cl.³ ............................................. A61F 13/00
[52] U.S. Cl. ..................................... 128/82; 128/83.5
[58] Field of Search ................ 128/83, 83.5, 85, 82; 2/2, 3

[56] References Cited

U.S. PATENT DOCUMENTS

| | | | |
|---|---|---|---|
| 3,263,679 | 8/1966 | Hass | 128/83.5 |
| 3,773,041 | 11/1973 | Bogar, Jr. et al. | 128/83.5 |
| 3,832,997 | 9/1974 | Cappelletti | 128/85 |
| 3,916,538 | 11/1975 | Loseff | 128/83.5 |
| 3,986,502 | 6/1975 | Gilson | 128/83.5 |
| 4,005,704 | 9/1975 | Stohr et al. | 128/83.5 |
| 4,061,138 | 12/1977 | Bernstein | 128/82 |
| 4,178,925 | 3/1978 | Hirt | 128/83.5 |

Primary Examiner—John D. Yasko

[57] ABSTRACT

A wrap-around protective device for the human toes when the foot is encased in an orthopedic cast comprising; a main part called a wrap, positioned against the outer surface of said cast in a horizontal plane, from one ankle bone foreward, arcing around the toes, and backward to the ankle bone on the other side of said casted foot, located fore and aft by two cross-pieces fastened to said wrap called bows, being of an arcuate shape to fit the contour of the underside of said cast that fit tightly against the front and rear surfaces of the rubber protrusion beneath said cast while the entire unit is removably held firm to said cast by means of laces that are fastened to said toe protector and tied together at the top surface of the part of the cast covering said foot.

5 Claims, 9 Drawing Figures

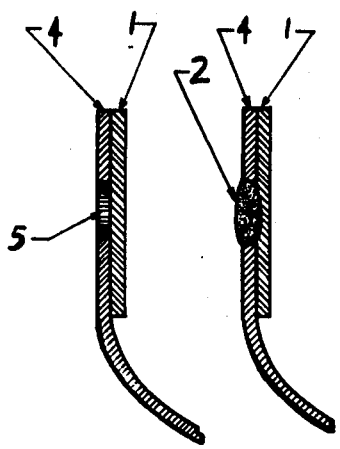
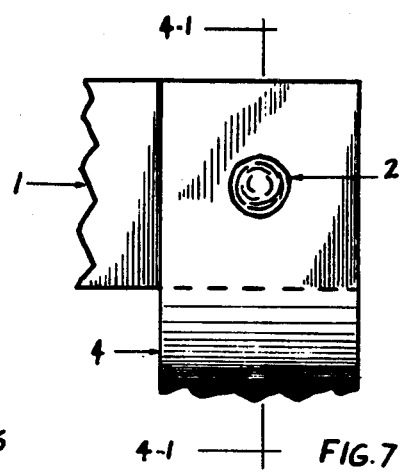
FIG. 5   FIG. 6   FIG. 7
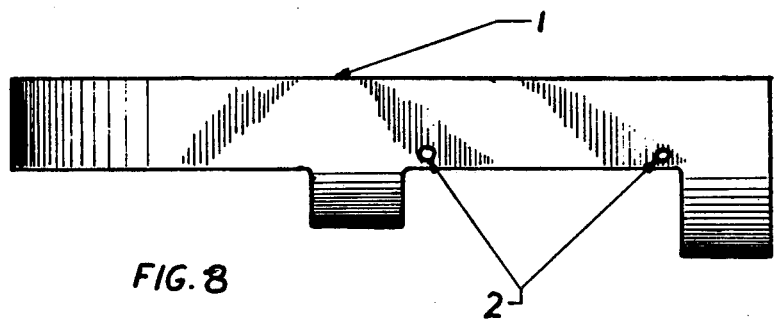
FIG. 8

TOE PROTECTOR FOR AN ORTHOPEDIC FOOD CAST

FIELD OF INVENTION

This invention relates to orthopedic foot casts, (commonly called walking casts), and more specifically to an improved toe protective device as an addition to said cast.

DISCUSSION OF PRIOR ART

Heretofore, toe protective devices employed usually served a compromise between foot support and toe protection or a dependancy on the construction of a special cast, or a special type of walker on the cast to be used for mounting and adjusting the toe protective device to fit properly. For example, U.S. Pat. No. 3,773,041, Bogar, Jr., et al. depends upon a special cast and a special walking tip, (or walker), to utilize the "toe guard". This unit leaves the toes exposed, yet provides a protective bar around toes, which are desireable features but the method of utilization is more complicated than it needs to be.

Another example is U.S. Pat. No. 4,061,138, Berstein, wherein the toe protective device provides a flat foot support and toe protective enclosure; said device must be built into the cast. Said device is in constant contact with the toes, which is not desireable, wherein the part the toes rest upon collects dust and dead skin debris, which increases the chance of infection.

The advantages of the present invention are;

1. The present toe protector will mount upon a common orthopedic walking cast with no modification to said cast.
2. Said toe protector provides desired exposure of the toes, yet provides very good protection for the toes.
3. Said toe protector is easily removed for inspection of the toes and toe area.
4. Said toe area is kept more sanitary, wherein said toe protector does not contact said toes.
5. Said toe protector of the present invention is subsequently easiest to use for both patient and doctor.

OBJECT OF THE INVENTION

This invention is a device which is generally an addition to an orthopedic cast for the human foot; to serve as a wrap-around bumper for protection of the toes, which are not covered by said cast.

The main object of the invention is to provide a simple, lightweight and effective toe protection apparatus attached to said cast and subsequent use thereof.

Another object of the invention is that it is easily removable; (being fastened to the cast with laces), to make post-operative inspection of the toes and toe area easier.

Another object of the invention is to be useable on either foot, as its shape is symmetrical.

A further object of the invention is that while providing protection for said toes, the toe protector does not cover or restrict said toes.

SUMMARY OF INVENTION

The embodiment of a wrap-around toe protector of the present invention includes a frame of three parts; the main part called a wrap, and two cross-pieces called bows. The bows are of an arcuate shape to fit the underside of the walking cast. The bows are fastened to said wrap by welds or rivets and serve to locate said wrap to said cast by fitting tightly against the front and rear sides of the rubber block (called a walker) on the underside of said cast. The wrap then extends, in a horizontal plane, from the ankle bone area forward, arcing around the toes, allowing clearance for said toes, and extending along the other side of said cast, ending at the ankle bone area. This protective apparatus is held firm to said cast by laces, similar to those used on boots. Said toe protective apparatus is constructed of aluminum sheet metal in the main embodiment, however, it may also be constructed of other metals, plastics, or other practical material.

This toe protective apparatus will accomplish the objects mentioned before, and said device will meet my claims and advantages described herein which will be fully understood by anyone skilled in the art, with reference to claims, and the accompanying drawings being a part thereof.

BRIEF DESCRIPTION OF THE DRAWINGS

FIGS. 5, 6, and 7 are enlarged views relating to the intersection of parts 1 and 4 at the left rear of said toe protector.

FIG. 8 is the side view of the toe protector in another embodiment.

DETAILED DESCRIPTION OF THE DRAWINGS

Figure 1:
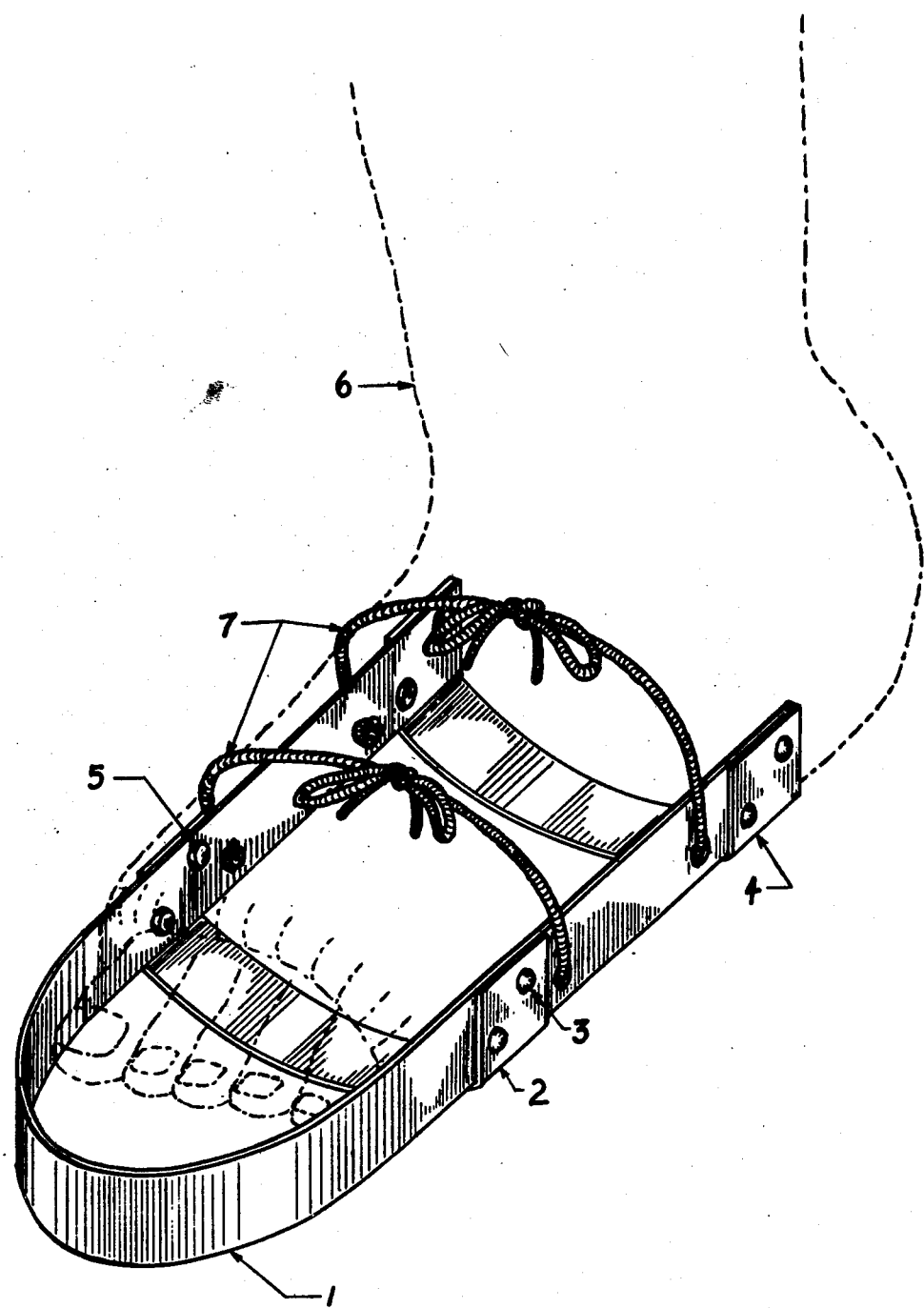
FIG. 1 is a perspective view of the wrap-around toe protective device with the casted foot shown in phantom.
Figure 2:
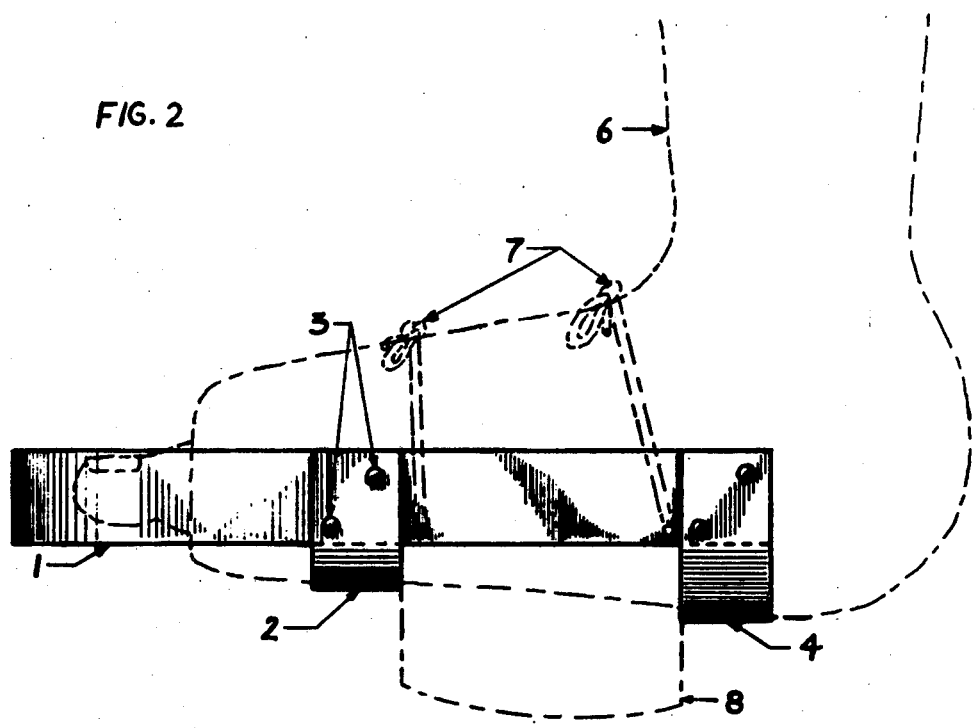
FIG. 2 is the side view of said apparatus with said casted foot shown in phantom.
Figure 3:
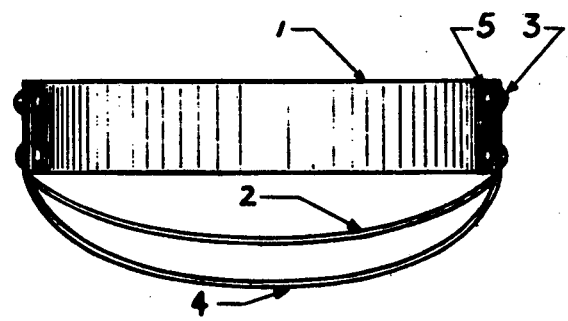
FIG. 3 is the rear view of said toe protector.
Figure 4:
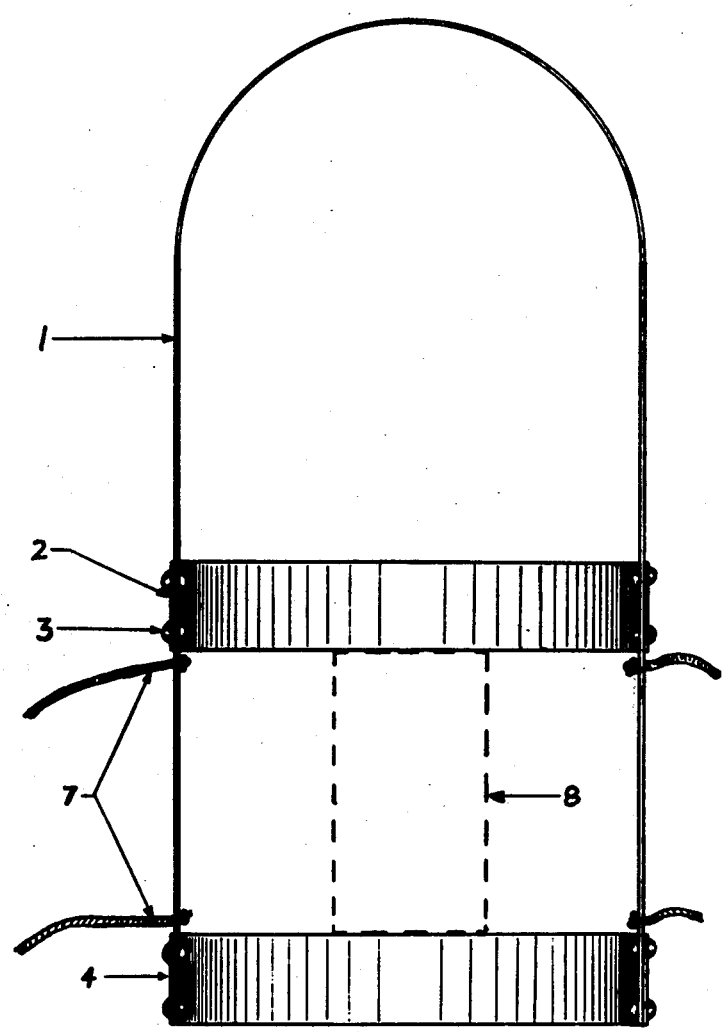
FIG. 4 is the top view of said toe protector with the walker (part of said cast) shown in phantom.

Referring more specifically to the drawings, wherein all reference numerals are constant throughout the five drawing sheets, reference numeral 1 designates the wrap, numeral 2 designates the front bow, numeral 4 designates the rear bow, and numeral 7 designates the laces. Said parts 1, 2, 4, and 7 comprise the toe protective invention. The cast, to which the toe protector is mounted is designated numeral 6, while the walker, being permanently affixed to, and part of said cast is designated numeral 8.

Said protective wrap 1 is formed of a strip of aluminum, as are the bows, 2 and 4, for the obvious advantage of using a lightweight, yet strong material. Said wrap 1 is formed to the desired shape to fit around the sides and front of said cast 6, wherein size depends upon the size grouping of said cast 6, which will be small, medium, or large. Said wrap 1 then fits closely against said cast 6, while leaving space at the front of said cast 6 wherein the toes, which protrude from the front of said cast 6 do not come in contact with said wrap 1.

The front bow 2, and the rear bow 4 is then formed (according to the size group of cast 6 to be fitted), to the desired size and shape to fit the underside of said cast 6, wherein the front bow 2 fits the contour of the underside of said cast 6 adjacent to the front surface of the walker 8, while rear bow 4 fits said underside adjacent to the rear surface of walker 8. Rivets 3 are then installed as means of permanent fixation of parts 2 and 4 to part 1, herein driven head of said rivets designated numeral 5.

Said laces 7 are installed therein through holes 12 in the sides of said wrap 1, wherein said laces 7 are secured by means of a knot, to be hidden between said cast 6 and said wrap 1.

Upon mounting the toe protector to said cast 6, the bows 2 and 4 can be bent by hand to widen or narrow the distance between the sides of said wrap 1 to achieve a more perfect fit, which may be necessary, wherein hand-lay-up of said cast 6 results in slightly varied outer demensions of said cast 6. Said bows 2 and 4 fit closely adjacent to said walker 8, therefore ensuring proper location of said toe protector, wherein said laces 7 are tied, said toe protector being firmly affixed to said cast 6.

As mentioned herein, the embodiment of the present invention includes construction materials of aluminum with parts being riveted as a means to permanently affix them together, numerous variations of said toe protector would readily occur to those skilled in the art, for example, referring to sheet 4, FIGS. 5, 6, and 7 show a weld 21 affixing the wrap 1 and rear bow 4. FIG. 5 is a cut-away view along line 4-1 of FIG. 7 and shows a hole 15 in said bow 4, while FIG. 6 shows the same view wherein said weld 21 has been performed, while FIG. 7 shows finished weld 21 at the intersection of parts 4 and 1 at the right rear of said toe protector. Further, said toe protector may not only be constructed of aluminum, wherein other metals may be deemed desireable as well.

Figure 9:
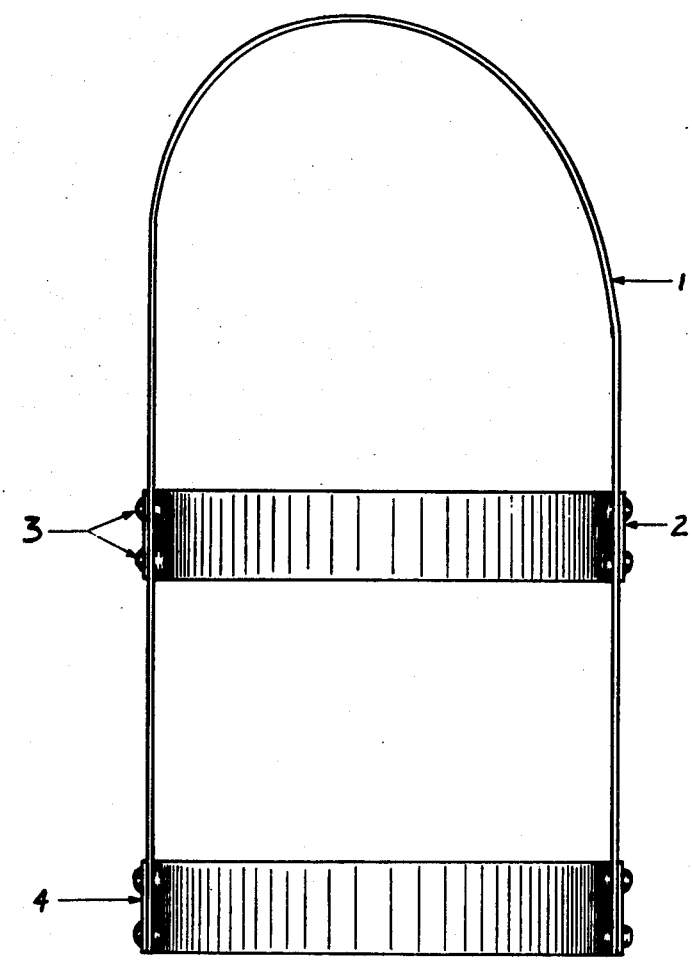
FIG. 9 is the top view of the toe protector in yet another embodiment.

Another variation is shown in FIG. 9, wherein in this top view, said wrap 1 has been altered in its shape, wherein instead of being symmetrical to fit either casted foot, said toe protector fits the contour of a right casted foot. In this embodiment, left and right wraps would be the deviation from the preferred embodiment.

Another variation of the toe protector, referring to FIG. 8, wherein said invention is casted of a polymeric substance, such as polyethylene or polystyrene.

Since numerous other modifications of said invention such as materials of construction, variations of the basic shape and/or contours will readily occur to those skilled in the art, it is not desired to limit the invention to the exact embodiment shown and described herein and all suitable equivalents are deemed to fall within the scope of the invention.

I claim:

1. A wrap-around toe protector as an addition to an orthopedic cast for the human foot comprising a frame of three parts assembled to be one piece consisting of a main part, the wrap, which is located along the sides and front of said cast in such position as to extend in a horizontal plane from the ankle area on one side of the casted foot, foreward, arcing around the toe area, then rearward, ending at the ankle area on the opposite side of said cast, and two secondary parts, the bows, which arc under said cast wherein both ends of said bows are permanently affixed to said wrap, forming a one-piece unit.

2. The apparatus of claim 1 wherein said bows provide means of locating said toe protector by fitting tightly against the front and rear surfaces of the walker, which is part of said cast.

3. The apparatus of claim 1 wherein the width and strength of said wrap is adequate to protect the toes.

4. The apparatus of claim 1 wherein said toe protector is made of metallic substance.

5. The apparatus of claim 1 wherein a means is provided to removably affix said toe protector to said cast by use of laces.

* * * * *